(12) United States Patent
Meyer et al.

(10) Patent No.: US 7,704,371 B2
(45) Date of Patent: Apr. 27, 2010

(54) CORROSION IDENTIFICATION AND MANAGEMENT SYSTEM

(75) Inventors: Eric S. Meyer, Chesterfield, MO (US); Jeffrey S. Sermersheim, St. Charles, MO (US); Stephen P. Gaydos, St. Louis, MO (US); Ko-Wei Liu, Seal Beach, CA (US)

(73) Assignee: The Boeing Company, Chicago, IL (US)

( * ) Notice: Subject to any disclaimer, the term of this patent is extended or adjusted under 35 U.S.C. 154(b) by 806 days.

(21) Appl. No.: 11/609,179

(22) Filed: Dec. 11, 2006

(65) Prior Publication Data

US 2008/0126033 A1    May 29, 2008

Related U.S. Application Data

(60) Provisional application No. 60/823,537, filed on Aug. 25, 2006.

(51) Int. Cl.
    *C23F 13/04*      (2006.01)
    *C23F 13/22*      (2006.01)

(52) U.S. Cl. .................. 205/725; 205/775.5; 324/71.2; 324/71.1; 324/700; 702/31; 702/32; 702/34; 702/189; 703/2

(58) Field of Classification Search ............... 324/71.1, 324/71.2, 700; 205/725, 775.5; 702/31, 702/32, 34, 189; 703/2
See application file for complete search history.

(56) References Cited

U.S. PATENT DOCUMENTS

| | | | |
|---|---|---|---|
| 6,195,624 B1 * | 2/2001 | Woodman et al. | 703/7 |
| 6,320,395 B1 * | 11/2001 | Bosch et al. | 324/700 |
| 6,811,681 B2 * | 11/2004 | Dowling et al. | 205/725 |
| 6,862,539 B2 * | 3/2005 | Fields et al. | 702/42 |
| 7,029,569 B2 * | 4/2006 | Dowling et al. | 205/725 |

* cited by examiner

*Primary Examiner*—Bruce F Bell
(74) *Attorney, Agent, or Firm*—McNees Wallace & Nurick, LLC

(57) ABSTRACT

The present invention is directed to a system for identifying and managing corrosion and methods related thereto. In particular, the invention provides a system for identifying and managing the structural corrosion potential for an assembly by measuring a "Relative Corrosion Index" ("RCI").

28 Claims, 8 Drawing Sheets

FIG. 8

CORROSION IDENTIFICATION AND MANAGEMENT SYSTEM

CROSS REFERENCE TO RELATED APPLICATIONS

This application claims the benefit of U.S. Provisional Patent Application No. 60/823,537, filed Aug. 25, 2006, which is incorporated herein by reference.

FIELD OF THE INVENTION

The present invention is directed to a system for identifying and managing corrosion and methods related thereto. In particular, the invention provides a system for identifying and managing the structural corrosion potential for an assembly by measuring a "Relative Corrosion Index" ("RCI").

BACKGROUND OF THE INVENTION

Corrosion is the deterioration of a material or its properties due to its reaction with the environment, typically resulting in the loss of structural integrity. It is estimated that an amount equal to about 3 to 4% of the GNP of industrialized countries is related to economic losses from corrosion, due to material loss, structural failure, loss of inventory, manufacturing plant down-time, warranty and insurance claims, lowered efficiency, contamination, and over designing of structures and components. Approximately 20% of life-cycle costs associated with the maintenance of military and commercial aircraft are related to corrosion inspection and repair. Corrosion also may lead to personal injury, property damage, and environmental contamination because of catastrophic degradation and failure of critical safety components. In addition, corrosion generates potentially detrimental and unnecessary ecological exploitation through the increased use of natural resources, both energy resources and material resources.

Current manufacturing and design practices rely on the personal knowledge, skill, and expertise of Material & Process Engineers to interrogate drawings and specifications on a part-by-part basis in order to identify possible corrosion issues. This engineering discipline is not systematic, and the engineering process lacks a common reference set of corrosion parameters. There exists a need for a quantitative tool to identify, characterize, and manage potential sites of corrosion.

SUMMARY OF THE INVENTION

Corrosion can occur through chemical or electrochemical reactions and is usually an interfacial process between a material and its environment. Deterioration solely by physical means such as erosion, galling, or fretting is not generally considered corrosion, but the surface damage caused by these processes may accelerate corrosion. Chemical corrosion may be a heterogeneous reaction that occurs at the material/environment interface and involves the material (such as a metal or composite material) itself as one of the reactants. Such occurrences may include materials in acidic or alkaline solutions, high-temperature oxidation environments, or in the presence of atmospheric oxygen and ambient water. Electrochemical corrosion consists of two or more partial reactions involving the transfer of electrons or charges. An electrochemical reaction requires an anode, a cathode, and a complete electric circuit, which may include a liquid electrolyte solution. For example, in the reaction of a metal in hydrochloric acid, the metal is oxidized and electrons are generated at the anode. At the same time, hydrogen cations are reduced and electrons are consumed to evolve hydrogen gas at the cathode. Generally, oxidation occurs at the anode, while reductions occur at the cathode. Corrosion usually occurs at the anode where the material (e.g., metal or alloy) is oxidized; this causes dissolution, wastage, penetration into the material, and loss of structural integrity.

For an anodic oxidation reaction of material to occur, a simultaneous reduction must take place. In corroding assemblies, the anodic and cathodic half-reactions are mutually dependent and form a galvanic cell. A material establishes an electrical potential or emf with respect to its environment and is dependent on the ionic strength and composition of the electrolyte, the temperature, the material (e.g., metal or alloy) itself, and other factors. The potential of a material at the anode in solution arises from the release of positively charged cations. The standard potential of a material is defined by fixing the equilibrium concentration of its ions at unit activity and under reversible and standard conditions (1 atm pressure, 25° C.), as is well known in the art. The potential, a measure of the thermodynamic driving influence of an electrochemical reaction, cannot be evaluated in absolute terms, but is determined by the difference between it and another reference electrode. Common standard reference electrodes used are saturated calomel electrode and saturated $Cu/CuSO_4$, whose potentials are measured relative to a standard hydrogen electrode, which by definition is 0.000V under standard conditions. The potential of a galvanic cell is the sum of the potentials of the anodic and cathodic half-cells in the environment surrounding them.

When designing an assembly with metal components, it is common engineering practice to refer to qualitative material compatibility charts such as that depicted in FIG. 1, which illustrates the compatibility of a first metal (102) with a second metal (104) in seawater (106). Similar compatibility charts for different environments are known in the art. In FIG. 1, two vectors of metal components are aligned along two sides of a triangle (110), in order from active metals (112) to less active metals (114). The metals A through T are identified in the Table (120). Using such a chart, an engineer may determine that platinum (122) and zinc (124) are "incompatible" (126) with each other in a seawater environment, whereas cadmium (132) and zinc (124) are "compatible" (138). This chart only provides information regarding the compatibility of two metal components in an electrolytic solution, that is, information about the likelihood of electrochemical corrosion, whereas it is not intended to predict the compatibility of the two metals in direct contact with each other. Furthermore, the information is not quantitative. A nominally quantitative assessment of the electrochemical reactivity of two metals may be determined by reference to FIG. 2, which is a galvanic series (200) of metals and alloys in seawater. For example, the electrochemical potential for platinum (214), cadmium (212), and zinc (210) versus a standard calomel reference electrode are illustrated. The difference in potential for a pair of metals in the series (200) may be used to calculate simple thermodynamic values associated with electrochemical corrosion of the metals in seawater, such as platinum-zinc or cadmium-zinc couples.

State of the art methods, however, lack a comprehensive tool to analyze arbitrarily complicated assemblies, particularly the quantitative assessment of the effects of surface protection, direct material-material contact, heat, ultraviolet light, moisture, the size and location of components, and other related parameters. The invention provides such a tool for the quantitative evaluation of material compatibility in the form of a Relative Corrosion Index, as described herein.

An advantageous embodiment of the invention is in the form of a computer program executed by a computer, such as a personal computer. The invention includes a knowledge-based system that contains subject-specific knowledge of one or more human experts, including the personal knowledge, skill, and expertise of Material & Process Engineers. The system is a program made up of a set of rules that analyze information supplied by the user of the system about specific classes of materials, as well as providing analysis of the problem(s), and, in some embodiments, recommending a course of user action in order to implement corrections in order to mitigate corrosion potential. Such a system may be valuable to organizations that have a high-level of knowledge and expertise that cannot be easily transferred to other members. The invention provides a mechanism for conveying the intelligence and information found in the intellect of experts and providing this knowledge to other members of an organization, such as a corporation or government entity, for problem-solving purposes. Some enterprises that may benefit from the invention include aircraft manufacturing and maintenance; oil drilling and transportation, including pipelines and off-shore drilling platforms; manufacture and maintenance of ocean-going cargo ships, railroads (including railcars), and automobiles and engines associated therewith; construction and inspection of bridges; building construction; construction and operation of pressure vessels (e.g., boilers); operation of petrochemical plants; and manufacture, operation, and inspection of tanks for storing and transporting toxic materials, among others.

In an embodiment of the invention, parameters that drive corrosion are identified and their relative contribution to accelerating corrosion have been integrated into a computer-based system, which is easily distributed. For example, a computer program may enable a user to calculate an RCI (Relative Corrosion Index) for an assembly using a single tool. An RCI summary may be provided for all combinations of materials, and it may be calculated based on material and environmental data entered by the user.

In another aspect, the invention further provides a method to convert an RCI to an inspection interval for an existing structure that has the potential for corrosion while in service. For example, the RCI for a component may be calculated, and an inspection scheme implemented in which those components that are determined to be more prone to corrosion are inspected more frequently. That is, the time period between inspections for a given component may be based on (e.g., proportional to) the magnitude of the RCI for that component. In this manner, time and costs associated with the inspection of various components within an aerospace vehicle may be managed. Accordingly, an example embodiment of the invention includes a method of inspecting an aerospace vehicle comprising determining the RCI for a component of the aerospace vehicle, inspecting the component for corrosion, and thereafter re-inspecting the component for corrosion, where the amount of time between lapsed before re-inspecting is based on the magnitude of the RCI for the component. For convenience, the terms component and assembly may be used interchangeably herein, and examples include a wing flap, cockpit instrument panel, toilet and lavatory facility, engine mount, landing gear, fuel system, exterior and interior fuselage, antenna, light fixture, window and door frame or fixture, and the like of an aerospace vehicle, such as an airplane.

In another aspect, the invention pertains to a method of preparing a maintenance schedule for an aerospace vehicle including calculating an RCI value for a component of an aerospace vehicle and assigning the frequency of scheduled inspection or maintenance of the component based on the RCI value.

Yet another embodiment of the invention includes a method of selecting a component for use in the manufacture or repair of an aerospace vehicle by calculating an RCI value for a component and selecting the component based on the RCI value, for example, where the RCI value falls within a predetermined range. Other embodiments of the invention include an aerospace vehicle having a plurality of components, each component having an RCI value falling within a predetermined range. Still another embodiment of the invention includes a component for an aerospace vehicle having an RCI value calculated according to the methods described herein.

In an example embodiment, the invention includes a method for computing the RCI for a structure comprising the steps of (1) identifying the materials used, including any organic surface treatments, inorganic surface finishes, coating damage potential, environmental conditions, and moisture intrusion potential; (2) calculating the galvanic coupling index based on the electrical potential of mating materials; (3) calculating the corrosion potential based on a system of scoring and modifying factors; and (4) normalizing the corrosion potential to fit to a predetermined RCI scale to produce an RCI value. The invention also includes the optional additional steps of (5) converting the RCI to an inspection interval; or (6) storing entered or calculated data or results, for example, in an electronic format, such as in a database.

In another embodiment, the invention includes a method for predicting corrosion potential for an assembly comprising from 1 to i materials, and from 0 to j interfaces, wherein each interface is a contact between any two materials. The method includes a step of calculating i $RCI_{Material}$ values, one value for each material, according to the following Formula: $RCI_{Material} = RCI_{Base} \times f_M(F_1^M, \ldots F_n^M)$ [Formula I], wherein $RCI_{Base}$ is a real number or a function that may be evaluated to a real number that is unique for the material, $f_M$ is a first scalar function (e.g., multiplication), and $F_1^M$ to $F_n^M$ are material corrosion factors selected from the set of real numbers or functions that may be evaluated to real numbers. The method also includes a step of calculating j $RCI_{Interface}$ values, one value for each interface, according to the following Formula: $RCI_{Interface} = RCI_{Material_{Max}} \times f_I(F_1^I, \ldots F_m^I)$ [Formula II], wherein $RCI_{Material_{Max}}$ is the largest $RCI_{Material}$ of the materials in the interface as calculated according to Formula I, $f_I$ is a second scalar function (e.g., multiplication), and $F_1^I$ to $F_m^I$ are interface corrosion factors selected from the set of real numbers or functions that may be evaluated to real numbers. The method further includes a step of calculating an $RCI_{Assembly}$ value according to the following Formula: $RCI_{Assembly} = f_A\{(RCI_{Material})_1, \ldots (RCI_{Material})_i, \ldots (RCI_{Interface})_j\}$ [Formula III], wherein $f_A$ is a third scalar function (e.g., the maximum), each $RCI_{Material}$ value is calculated according to Formula I, and each $RCI_{Interface}$ value is calculated according to Formula II.

The principles of the invention do not limit its implementation solely as a computer program, and the invention may be practiced with equal efficacy and value using alternative techniques.

Other features and advantages of the present invention will be apparent from the following more detailed description of the preferred embodiment, taken in conjunction with the accompanying drawings, which illustrate by way of example the principles of the invention.

BRIEF DESCRIPTION OF THE DRAWINGS

FIG. 8 is a graphical user interface of a computer program that calculates RCI values based on various input parameters.

DETAILED DESCRIPTION OF THE INVENTION

Figure 1:
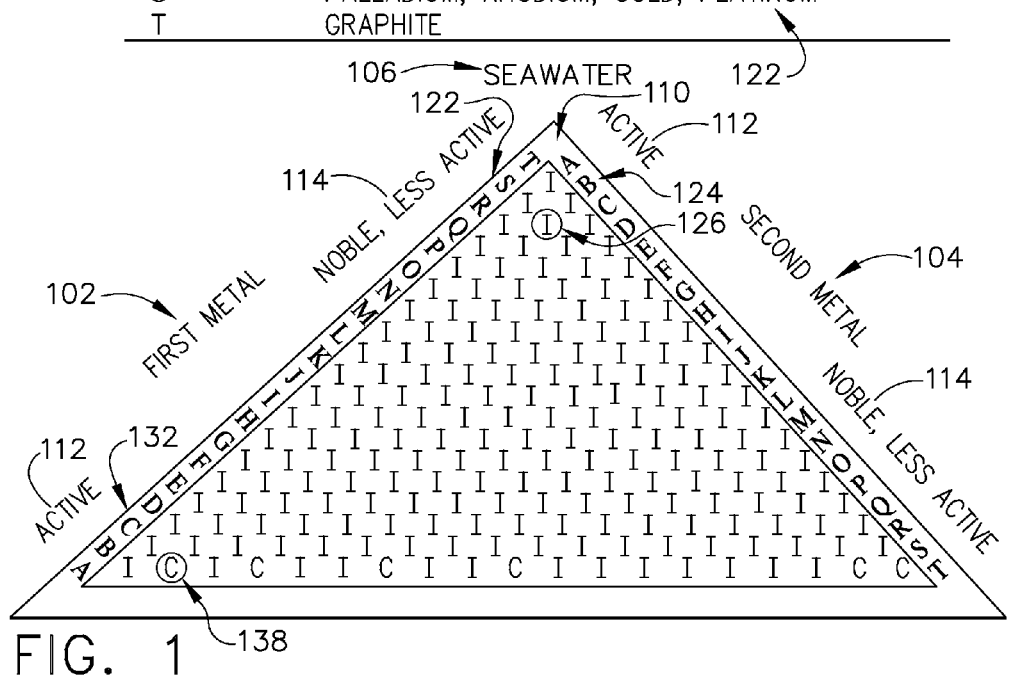
FIG. 1 is an example of a qualitative corrosion compatibility chart for two different metals in a seawater environment.
Figure 2:
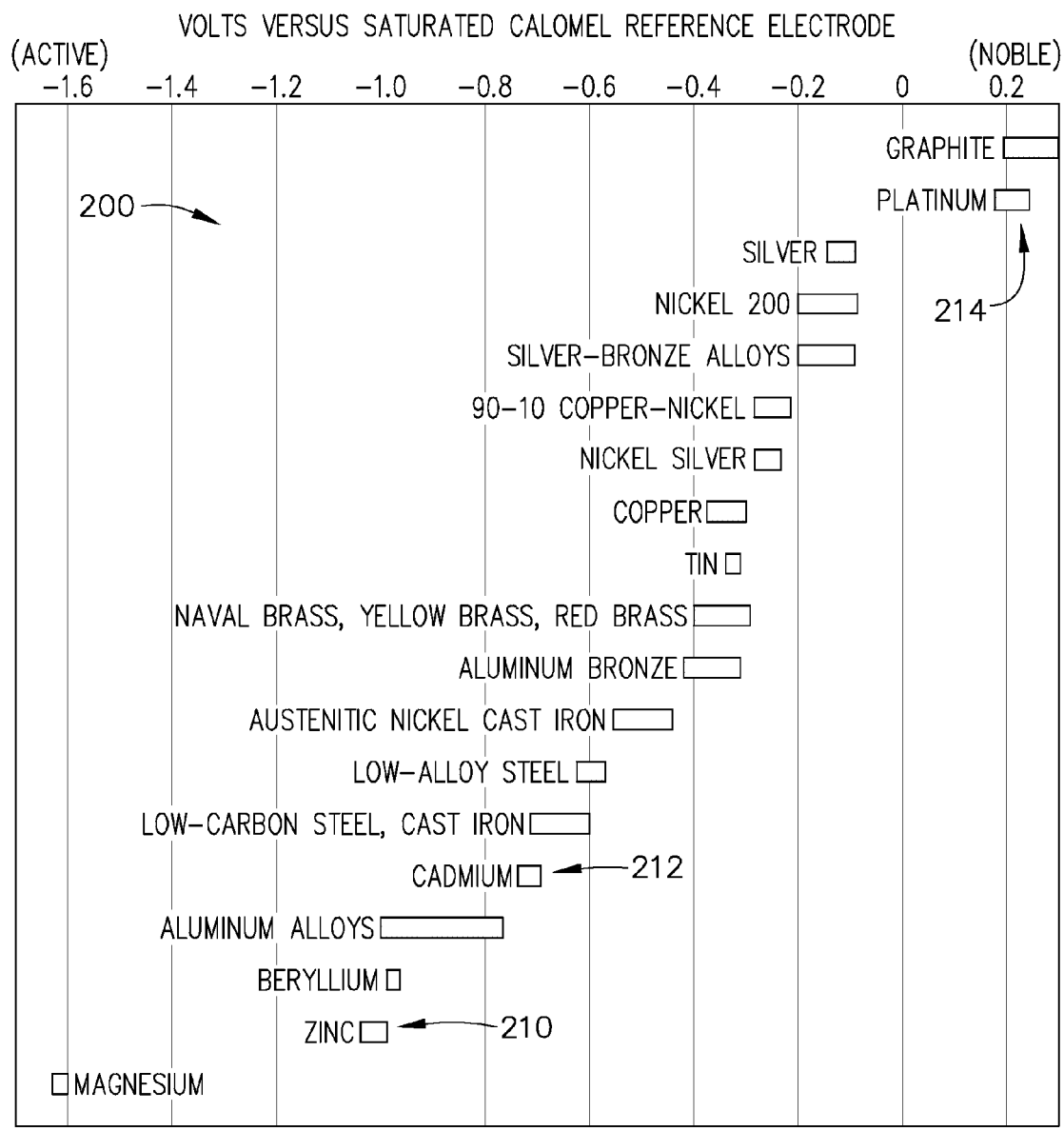
FIG. 2 is an example galvanic series of certain metals and alloys in seawater.
Figure 3:
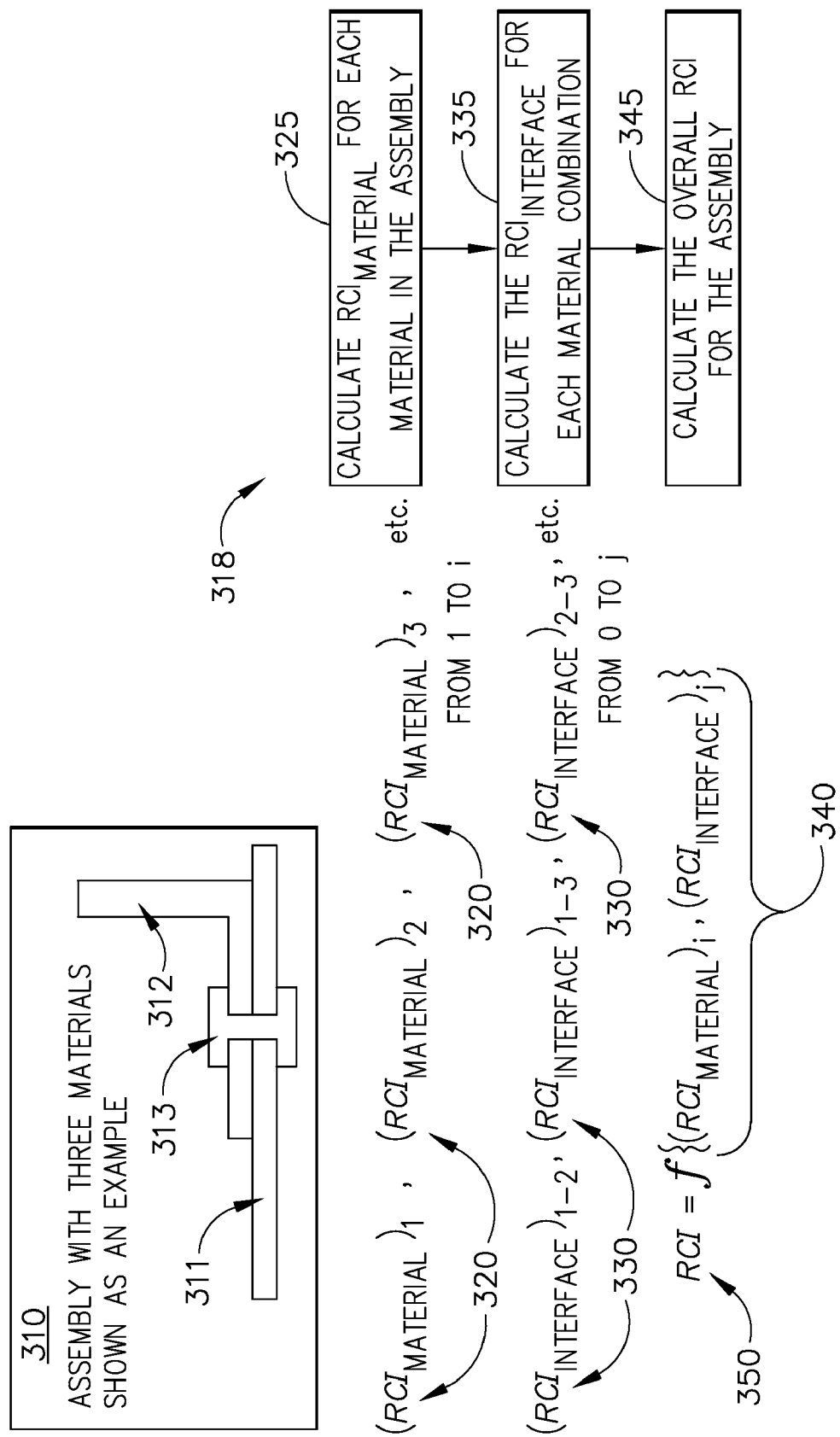
FIG. 3 illustrates how an RCI is calculated from $RCI_{Material}$ and $RCI_{Interface}$ values.

Referring to FIG. 3, as depicted in the flowchart (318), the overall RCI (350) for an assembly begins with the stepwise calculation of the $RCI_{Material}$ value (320) for each material in the assembly (325) and the $RCI_{Interface}$ value (330) for each material-material interface in the assembly (335), which steps may be completed in any order. After all of the $RCI_{Material}$ and $RCI_{Interface}$ values have been calculated, as described herein below, the overall RCI for the assembly is calculated (345). The RCI for the assembly is the maximum RCI value of the $RCI_{Material}$ (325) and $RCI_{Interface}$ (335) quantities. The overall RCI value (350) is a function (340) of the $RCI_{Material}$ (325) and $RCI_{Interface}$ (335) values, namely the maximum RCI of the materials and interfaces.

Still referring to FIG. 3, an example three-component assembly (310) is illustrated, which includes a flat metal sheet (311) and an angled metal sheet (312) joined by a metal fastener (313). This example three-component assembly (310) has three metal components (311, 312, 313), and therefore three $RCI_{Material}$ values (320). The three-component assembly (310) also has three metal-metal interfaces where the individual metal components touch each other, and therefore three $RCI_{Interface}$ values (330). In this example assembly (310), the RCI is the maximum of $(RCI_{Material})_1$, $(RCI_{Material})_2$, $(RCI_{Material})_3$, $(RCI_{Interface})_{1-2}$, $(RCI_{Interface})_{1-3}$, and $(RCI_{Interface})_{2-3}$. Although the illustrated assembly (310) has metallic components, the invention also pertains to other materials that may be susceptible to corrosion, for example, a metal fastener joining a graphite epoxy panel to an aluminum panel.

An example embodiment of the invention pertains to the analysis of a three component assembly as depicted in FIG. 3, but other embodiments of the invention include the study of arbitrarily large assemblies having from 1 to i $RCI_{Material}$ values for each component and from 0 to j $RCI_{Interface}$ values for each of the material-material contacts. An assembly having only one component has no interface. Overall RCI values range from about 0 to about 100, where RCI=0 is most preferred and RCI=100 is undesirable.

Figure 4:
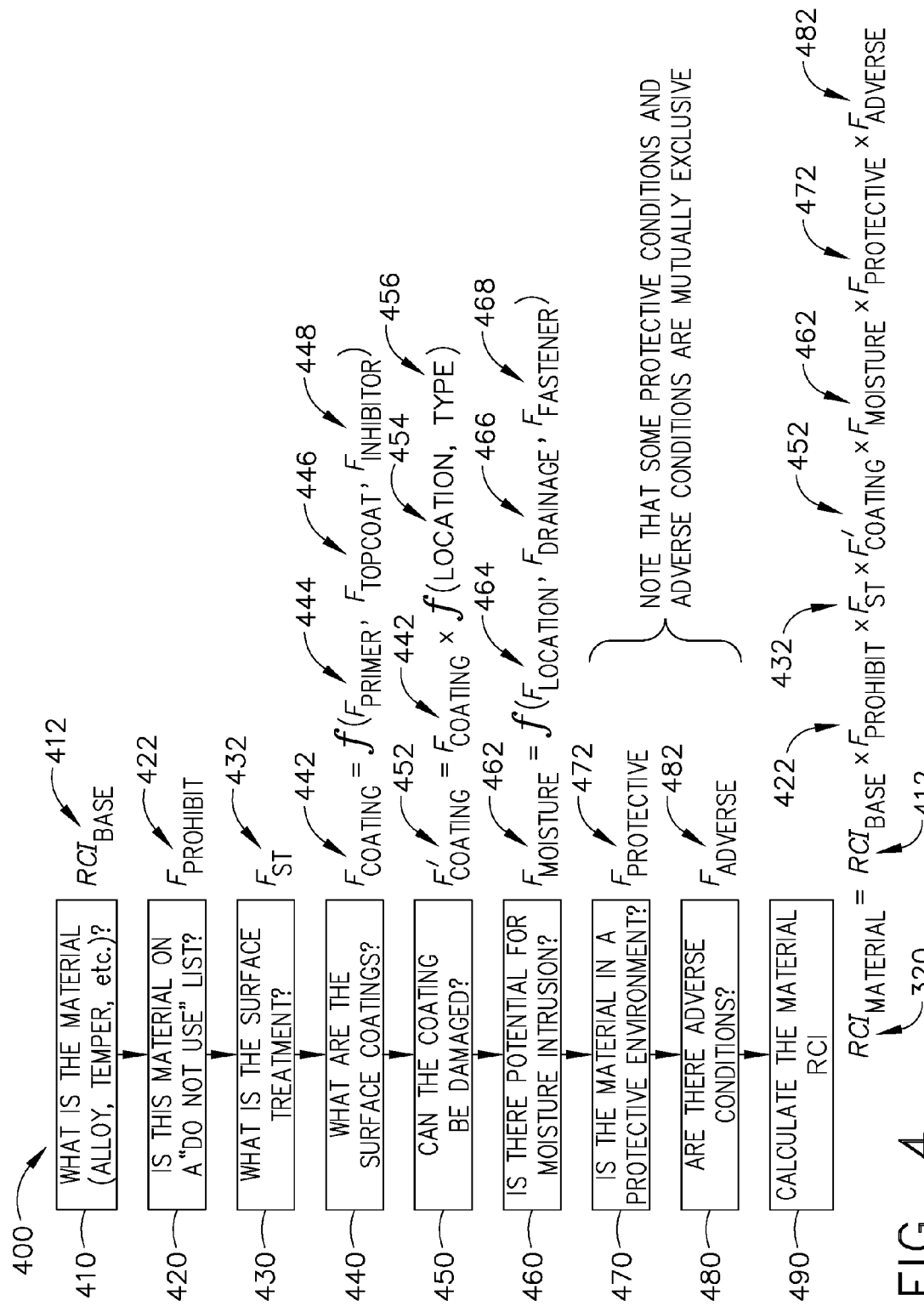
FIG. 4 illustrates how $RCI_{Material}$ values are calculated.

FIG. 4 illustrates how the $RCI_{Material}$ values (320) are calculated, including the steps illustrated in the flowchart (400). For each material, the type of material is identified (410) and assigned an $RCI_{Base}$ value (412) by referring to a ranked list of various materials. $RCI_{Base}$ values (412) are semi-empirically determined for each material. An example of a material and the corresponding $RCI_{Base}$ value is 2024-T3 with and $RCI_{Base}$ of 90.

Still referring to FIG. 4, if any material is prohibited (420), then an arbitrarily high $F_{Prohibit}$ value (422) is assigned such that the calculated $RCI_{Material}$ value (320) is 100, i.e., the maximum. If the material is not prohibited, then the $F_{Prohibit}=1$.

Still referring to FIG. 4, if the surface of the material has been treated or prepared by certain processes (430), then an $F_{ST}$ value (432) is assigned by referring to a ranked list of various surface treatments. $F_{ST}$ values (432) range from about 0 to about 1 and are semi-empirically determined for each surface treatment. If the material has no surface treatment, then the $F_{ST}=1$. An example surface treatment is nickel plate with an $F_{ST}$ of 0.15.

Still referring to FIG. 4, if the surface of the material has been coated (440), then an $F_{Coating}$ value (442) is calculated by referring to ranked lists of primers, topcoats, and inhibitors, and the $F_{Coating}$ value (442) is a function of all three of these parameters. Specifically, $F_{Coating}=f(F_{Primer}, F_{Topcoat}, F_{Inhibitor})$, where the function is multiplication. $F_{Primer}$ (444), $F_{Topcoat}$ (446), and $F_{Inhibitor}$ (448) values range from about 0 to about 1 and are semi-empirically determined for each primer, topcoat, and inhibitor. If a material lacks a primer, topcoat, or inhibitor, then the corresponding $F_{Primer}$, $F_{Topcoat}$, or $F_{Inhibitor}$ value is 1. If a material lacks a coating, then $F_{Coating}=1$, in which case the material may be in electrical contact with another material. Example primers and the corresponding $F_{Primer}$ values include an epoxy primer with and $F_{Primer}$ of 0.90. Example topcoats and the corresponding $F_{Topcoat}$ values include polyurethane with and $F_{Topcoat}$ of 0.20. An example inhibitors is hexavalent chromium with and $F_{Inhibitor}$ of 0.50.

Still referring to FIG. 4, if any coated material is situated in a location or environment where the coating may be damaged (450), for example, in the presence of sand, gravel, exhaust from combustion, and the like, then an $F'_{Coating}$ value (452) is calculated. $F'_{Coating}$ values range from about 0 to about 10 or greater. If a material is not coated, then $F'_{Coating}=1$, If a material is coated, then $F'_{Coating}$ (452) is a function of both the location (454) of a component, which is a measure of how exposed a component is to environmental or maintenance damage, and the type (456) of damage that may occur in that location, such as heat damage from jet engine exhaust, abrasion from impact with sand, or impact damage by incidental contact of tools during routine maintenance. $F'_{Coating}$ (452) is calculated by multiplying $F_{Coating}$ (442) by a factor assigned by reference to a table of ranked, semi-empirically determined values for particular locations (454) and types (456). In this context, "location" refers to where in the assembly a component is situated (top, bottom, etc.); location does not refer to geography.

Still referring to FIG. 4, if a material is in a location or environment where there is potential for moisture intrusion (460), then an $F_{Moisture}$ value (462) is calculated. $F_{Moisture}$ values range from about 0 to approximately 10 or greater. If moisture exposure is deemed not to be likely or is not important in calculating an RCI, then $F_{Moisture}=1$. If a material may be exposed to moisture, then $F_{Moisture}$ (462) is a function (multiplication) of the location, $F_{Location}$, (464) of a component, the drainage characteristics of that location, $F_{Drainage}$, (466), and whether the material is functioning as a fastener, $F_{Fastener}$, (468).

Still referring to FIG. 4, an assessment of whether the material is in a protective environment (470) or in adverse conditions (480) is made in order to calculate a $F_{Protective}$ value (472) or $F_{Adverse}$ value (482), as discussed in detail herein below. These two conditions are mutually exclusive. That is, if a material is deemed to be in a protective environment (e.g., submerged in oil), then a $F_{Protective}$ value (472) is calculated and $F_{Adverse}$=1. Likewise, if a material is deemed to be subject to adverse conditions (e.g., seawater), then a $F_{Adverse}$ value (482) is calculated and $F_{Protective}$=1. $F_{Adverse}$ values range from about 0 to approximately 10 or greater, whereas $F_{Protective}$ values range from about 0 to about 1. A factor that has no protective or adverse effects is unitary (equal to 1).

Still referring to FIG. 4, after the $RCI_{Base}$, $F_{Prohibit}$, $F_{ST}$, $F'_{Coating}$, $F_{Moisture}$, $F_{Protective}$, and $F_{Adverse}$ values have been determined, they are multiplied together to arrive at an $RCI_{Material}$ value (320) for a component in the final step (490). The process outlined in the flowchart (400) is repeated for each component of an assembly under evaluation. $RCI_{Material}$ values range from about 0 to about 100.

Figure 5:
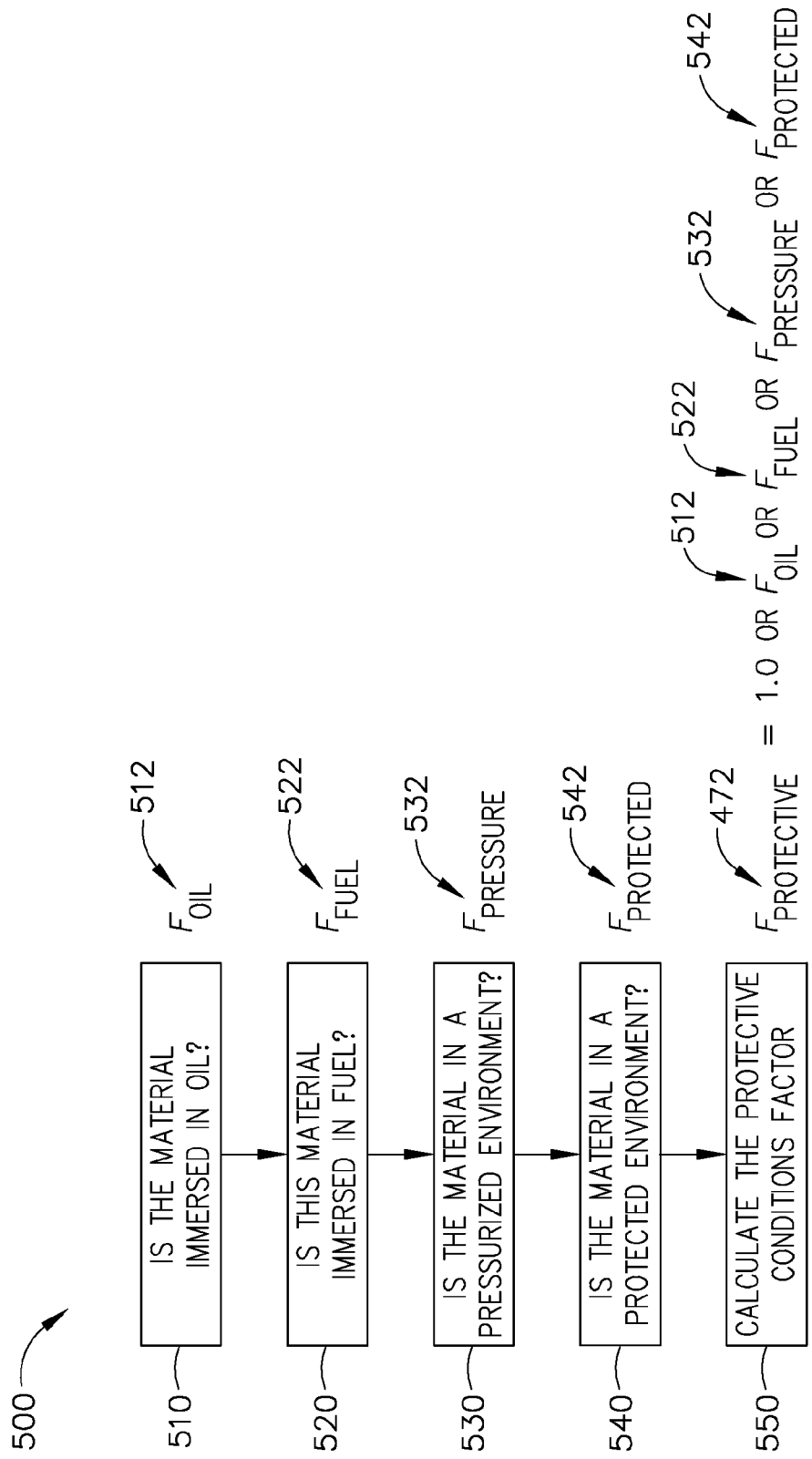
FIGS. 5 and 6 illustrate the parameters used in calculating $F_{Protective}$ and $F_{Adverse}$ values, respectively.

FIG. 5 illustrates how $F_{Protective}$ values (472) are calculated based on the environment(s) that a material will encounter while in service. Referring to the flowchart (500), a determination is made whether the material is immersed in oil (510), in which case an $F_{oil}$ value (512) is assigned by referring to a ranked list of oils. $F_{oil}$ values (512) are semi-empirically determined for each oil, and an example is hydraulic oil with an $F_{oil}$ of 0.10.

Still referring to FIG. 5, a determination is made whether the material is immersed in fuel (520), in which case an $F_{fuel}$ value (522) is assigned by referring to a ranked list of fuels. $F_{fuel}$ values (522) are semi-empirically determined for each fuel, and an example is jet fuel with and $F_{Fuel}$ of 0.10.

Still referring to FIG. 5, a further determination is made whether the material is in a pressurized environment (530), for example, whether a component is in the pressurized passenger compartment of an airplane, in which case an $F_{pressure}$ value (532) is assigned by referring to a ranked list of pressure conditions. $F_{pressure}$ values (532) are semi-empirically determined for each pressure condition, and an example is cockpit pressurization with an $F_{pressure}$ of 0.20.

Still referring to FIG. 5, yet a further determination is made whether the material is in a protected environment (540), for example, whether a component is in a hermetically sealed compartment, in which case an $F_{protected}$ value (542) is assigned by referring to a ranked list of protection conditions. $F_{protected}$ values (542) are semi-empirically determined for each condition, and an example is a sealed cargo container with an $F_{protected}$ of 0.01.

In carrying out the calculation depicted in FIG. 5, $F_{oil}$, $F_{fuel}$, $F_{pressure}$, and $F_{protected}$ conditions may be defined herein as being mutually exclusive. That is, $F_{protective}$, which ranges from about 0 to about 1, is either 1.0, $F_{oil}$, $F_{fuel}$, $F_{pressure}$, or $F_{protected}$.

Figure 6:
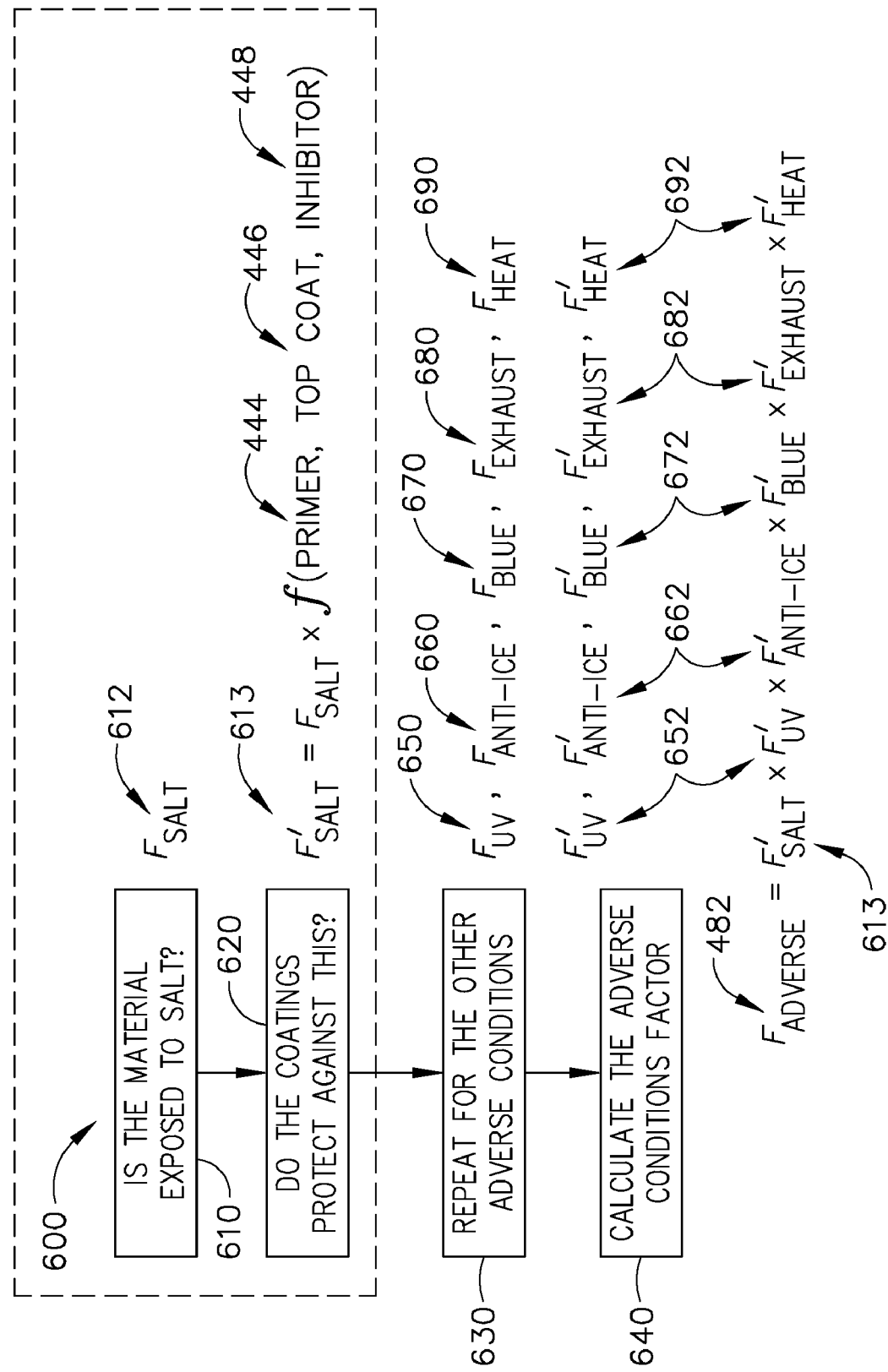

FIG. 6 illustrates the steps included in calculating $F_{Adverse}$ values (482), which may range from about 0 to approximately about 10 or greater. The steps are illustrated in the flowchart (600), and begin with ascertaining whether a material is likely to be exposed to certain adverse conditions. For each adverse condition, a semi-empirically determined F value is assigned for each condition, offset by the effects of any coating, and then multiplied to produce an $F_{Adverse}$ value (482). Examples of such adverse conditions and the corresponding F values include exposure to salt ($F_{salt}$=4) (612), ultraviolet light ($F_{UV}$=2) (650), aircraft deicing solution ($F_{Anti-ice}$=10) (660), aircraft toilet ("blue") waste water ($F_{Blue}$=8) (670), aircraft engine exhaust ($F_{Exhaust}$=2) (680), and heat greater than about 250° F. ($F_{Heat}$=2) (690). If one of these adverse conditions is determined not to be present, then it may be omitted from the calculation of $F_{Adverse}$. Likewise, if additional adverse conditions are present then corresponding F values for those conditions may be added to the calculation of $F_{Adverse}$. One skilled in the art will appreciate that the adverse conditions, while they have been described herein with reference to the aircraft industry, may be modified and adapted to a wide variety of engineering disciplines and industries.

Still referring to FIG. 6, if a material is likely to be exposed to salt (610), then the effects of any coating are evaluated (620). For example, if a material is exposed to salt, then the value of $F'_{salt}$ (613) is calculated using the same $F_{Primer}$ (444), $F_{Topcoat}$ (446), and $F_{Inhibitor}$ (448) factors described above with reference to FIG. 4, multiplied by $F_{salt}$ (612). The process is repeated (630) for other adverse conditions in order to calculate $F'_{UV}$ (652), $F'_{Anti-Ice}$ (662), $F'_{Blue}$ (672), $F'_{Exhaust}$ (682), and $F'_{Heat}$ (692). After all of the adverse condition factors have been calculated with respect to any coatings, they are multiplied together (640) to produce $F_{Adverse}$ (482).

Figure 7:
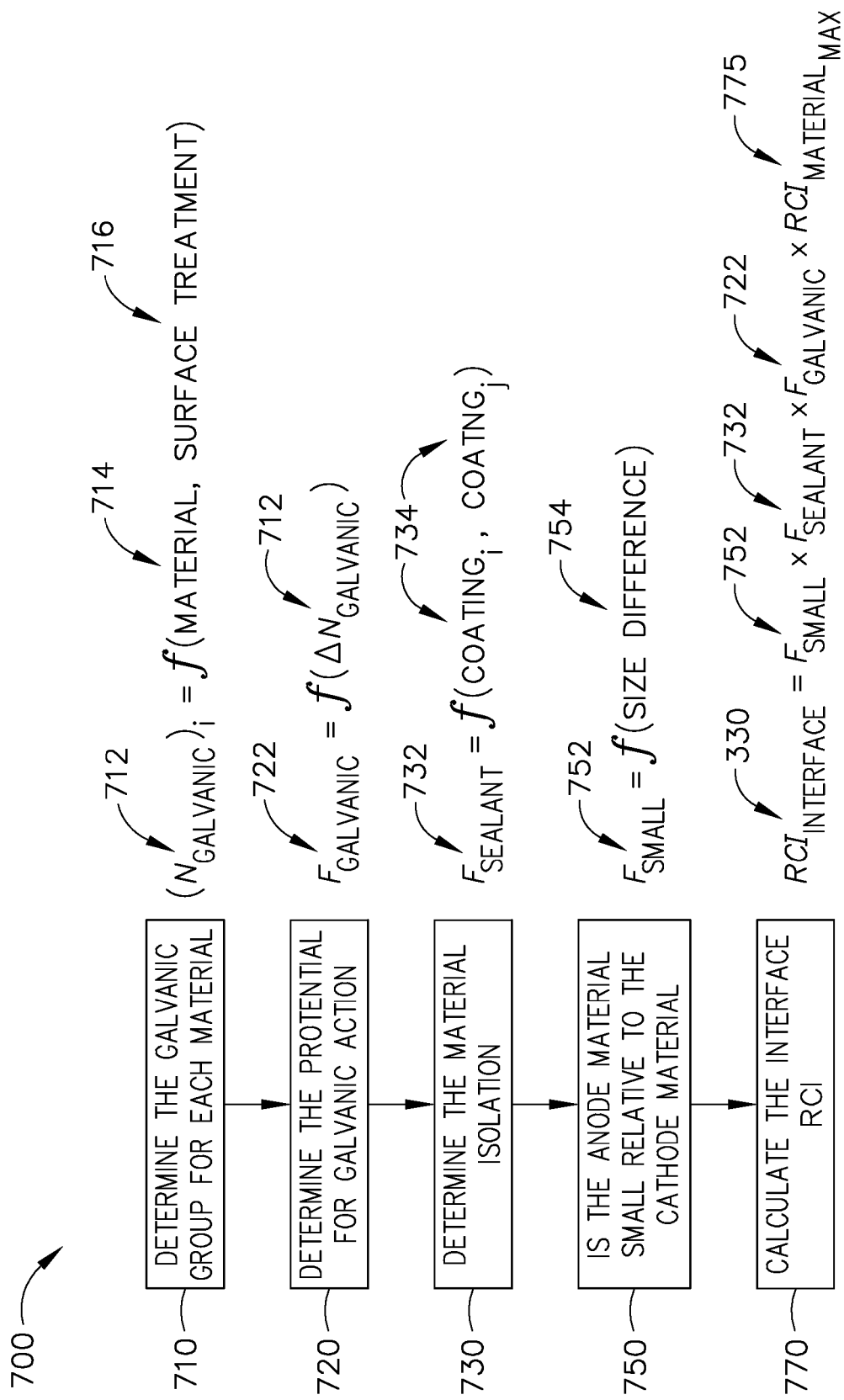
FIG. 7 illustrates how $RCI_{Interface}$ values are calculated.

The calculation of $RCI_{Interface}$ values (330) is illustrated in the flowchart (700) in FIG. 7. For each material in the interface, a galvanic group (712) is determined (710) and assigned a value and assigned an $RCI_{Base}$ value by referring to a ranked list of various materials classified according to the material type (714) and the surface treatment (716). $N_{galvanic}$ values (712) are related to the electrochemical potential for each material, and examples of $N_{galvanic}$ values (712) for particular materials include an $N_{galvanic}$ of 2 between an aluminum and a stainless steel.

Still referring to FIG. 7, the potential for galvanic action, $F_{galvanic}$, (722) is a function (720) of the difference in the two $N_{galvanic}$ values (712) for an interface. For example, when $N_{galvanic}$=2, $F_{galvanic}$ may be 6.

Still referring to FIG. 7, an isolation factor, $F_{Sealant}$ (732), is calculated (730) to account for whether the materials at an interface are electrochemically isolated from each other by means of a coating (734) on any of the components. $F_{Sealant}$ values (732) are semi-empirically determined for each condition, and examples of such conditions and the corresponding values include polysulfide sealant with an $F_{Sealant}$ of 0.1.

Still referring to FIG. 7, a further consideration is made (750) of the relative sizes of the components in an interface of any assembly. The purpose of this factor, $F_{small}$ (752), is to account for circumstances in which a small component is in contact with a significantly larger component. It is possible that a large size difference (754) of two dissimilar components (e.g., mass difference or surface area difference) may overwhelm the anodic capacity of the smaller component (the smaller component may be completely oxidized), resulting in an exaggerated corrosion effect. When small rivets or fasteners function as a sacrificial anode, they may completely corrode. If the relative sizes of the components is not important to the calculation of the $RCI_{Interface}$ value (330), then $F_{small}$=1. Example values of $F_{small}$ include 2.0.

Still referring to FIG. 7, consideration is made for interfaces in which a direct material-material contact exists (760). In such circumstances a complete electrical circuit may exist by which electrons flow from one conductive component to the other. When the interface forms an electrical bond between the components, $F_{Sealant}$ (732) and $F_{Coating}$ (442) should be equal to 1.

Finally, referring still to FIG. 7, the $RCI_{Interface}$ value (330) for each interface is calculated by multiplying $F_{small}$ (752), $F_{Sealant}$ (732), and $F_{galvanic}$ (722) by the largest $RCI_{Material}$ (775) of the materials involved in the interface. These steps are repeated for each interface present in the assembly.

Figure 8:
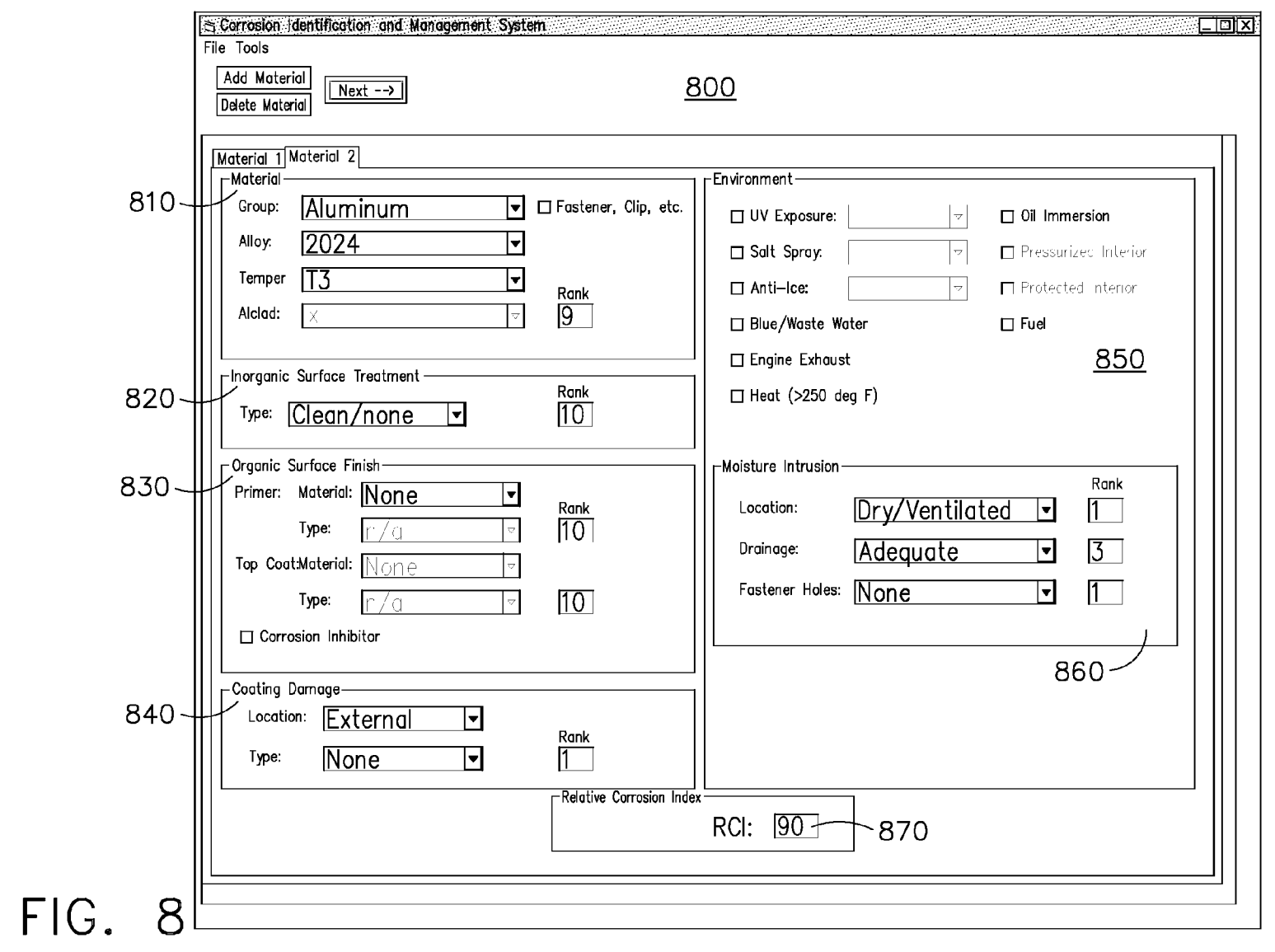

An example implementation of the invention includes a computer program product embodied on a computer readable medium and executable by a microprocessor for predicting corrosion potential incorporating computer instructions for executing the steps of the methods described herein. While it is preferred that the control algorithm be embodied in a computer program(s) and executed by the microprocessor, it is to be understood that the control algorithm may be implemented and executed using digital or analog hardware by those skilled in the art. FIG. 8 depicts a graphical user interface (800) by which a user may use the invention using a computer program executed on a computer. The interface permits the user to enter information about the type of material (810), the surface treatment (820), the surface finish such as a coating (830) and the exposure of such a coating to potential damage (840), the environment (850), and moisture (860). Data are entered by the user by drop-down menus and check boxes. The computer program calculates the RCI (870) as described herein. The RCI (870) may be used in evaluating engineering blueprints, design plans, and specifications for possible corrosion issues. In addition, the RCI for an existing structure may be used for designing an inspection regimen in which assemblies with a higher RCI are subject to more frequent inspection and assemblies with a lower RCI are inspected less frequently.

In yet another embodiment, the invention includes a general method for predicting corrosion potential for an assembly comprising from 1 to i materials, and from 0 to j interfaces, wherein each interface is a contact between any two materials. The method includes a step of calculating i $RCI_{Material}$ values, one value for each material, according to the following Formula: $RCI_{Material}=RCI_{Base} \times f_M(F_1^M, \ldots F_n^M)$ [Formula I], wherein $RCI_{Base}$ is a real number or a function that may be evaluated to a real number that is unique for the material, $f_M$ is a first scalar function (e.g., multiplication), and $F_1^M$ to $F_n^M$ are material corrosion factors selected from the set of real numbers or functions that may be evaluated to real numbers. The method also includes a step of calculating j $RCI_{Interface}$ values, one value for each interface, according to the following Formula: $RCI_{Interface}=RCI_{Material_{Max}} \times f_I(F_1^I, \ldots F_m^I)$ [Formula II], wherein $RCI_{Material_{Max}}$ is the largest $RCI_{Material}$ of the materials in the interface as calculated according to Formula I, $f_I$ is a second scalar function (e.g., multiplication), and $F_1^I$ to $F_m^I$ are interface corrosion factors selected from the set of real numbers or functions that may be evaluated to real numbers. The method further includes a step of calculating an $RCI_{Assembly}$ value according to the following Formula: $RCI_{Assembly}=f_A\{(RCI_{Material})_1, \ldots (RCI_{Material})_i, \ldots (RCI_{Interface})_j\}$ [Formula III], wherein $f_A$ is a third scalar function (e.g., the maximum), each $RCI_{Material}$ value is calculated according to Formula I, and each $RCI_{Interface}$ value is calculated according to Formula II. According to the method, the magnitude of $RCI_{Assembly}$ is based on the corrosion potential of said assembly. The term "scalar function" is intended to include any mathematical function in which one or more operands are evaluated to produce a single dimensionless numerical value, such as multiplication.

In an example embodiment, the material corrosion factors and the interface corrosion factors include protective corrosion factors and adverse corrosion factors. The protective corrosion factors may be real numbers or functions that may be evaluated to real numbers. Similarly, the adverse corrosion factors may be real numbers or functions that may be evaluated to real numbers. In a preferred embodiment, the protective corrosion factors and the adverse corrosion factors are selected from orthogonal sets, i.e., sets that only have one point in common. For example, the protective corrosion factors may be from 0 to 1, and the adverse corrosion factors may be from 1 to about 100, and therefore the two sets share the common value 1. The principles of the invention may be adapted to include other sets, such as protective corrosion factors selected from zero and negative numbers, and adverse protection factors may be zero and positive numbers.

While the invention has been described with reference to a preferred embodiment, it will be understood by those skilled in the art that various changes may be made and equivalents may be substituted for elements thereof without departing from the scope of the invention. For example, the particular numerical calculations described herein are scaled to particular ranges, for example the RCI for an assembly is between about 0 and about 100, with 0 be unlikely to corrode and 100 being very likely to corrode. As described herein, "beneficial" factors (such as the presence of a sealant or coating on a material) are incorporated into RCI calculations as factors having values less than 1. Similarly, "detrimental" factors (such as the presence of salt) are incorporated into RCI calculations as factors having values greater than 1. One skilled in the art will readily appreciate that these ranges and calculations may be modified to suit particular needs. For example, the calculations described herein may be readily modified to produce an RCI scale ranging from negative values to positive values. Further such modifications will be readily appreciated by the skilled artisan. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method comprising a computer programmed product embodied on a computer readable medium and configured to execute by microprocessor a method for predicting corrosion potential comprising instructions for executing the steps of providing an assembly comprising from 1 to i materials, and from 0 to j interfaces, wherein each interface is a contact between any two materials;

calculating an $RCI_{Material}$ value for each material according to Formula I:

$$RCI_{Material}=RCI_{Base} \times f_M(F_1^M, \ldots F_n^M) \qquad \text{[Formula I]}$$

wherein $RCI_{Base}$ is a real number or a function that may be evaluated to a real number that is unique for the material, $f_M$ is a first scalar function, and $F_1^M$ to $F_n^M$ are material corrosion factors selected from the set of real numbers or functions that may be evaluated to real numbers;

calculating an $RCI_{Interface}$ value for each interface according to Formula II:

$$RCI_{Interface}=RCI_{Material_{Max}} \times f_I(F_1^I, \ldots F_m^I) \qquad \text{[Formula II]}$$

wherein $RCI_{Material_{Max}}$ is the largest $RCI_{Material}$ of the materials in the interface as calculated according to Formula I, $f_I$ is a second scalar function, and $F_1^I$ to $F_m^I$ are interface corrosion factors selected from the set of real numbers or functions that may be evaluated to real numbers; and calculating an $RCI_{Assembly}$ value according to Formula III:

$$RCI_{Assembly} = f_A\{(RCI_{Material})_1, \ldots (RCI_{Material})_i, \ldots (RCI_{Interface})_j\} \quad \text{[Formula III]}$$

wherein
$f_A$ is a third scalar function,
each $RCI_{Material}$ value is calculated according to Formula I, and
each $RCI_{Interface}$ value is calculated according to Formula II;
wherein the magnitude of $RCI_{Assembly}$ is based on the corrosion potential of said assembly.

2. The method according to claim 1, wherein said material corrosion factors and said interface corrosion factors include protective corrosion factors and adverse corrosion factors, wherein said protective corrosion factors are selected from a first set consisting of real numbers or functions that may be evaluated to real numbers and said adverse corrosion factors are selected from a second set consisting of real numbers or functions that may be evaluated to real numbers, wherein said first set and said second set are orthogonal.

3. The method according to claim 2, wherein said first set consists of real numbers less than or equal to one, and said second set consists of real numbers greater than or equal to one.

4. The method according to claim 1, wherein said first scalar function is multiplication, and wherein said second scalar function is multiplication.

5. The method according to claim 1, wherein said third scalar function is a maximum function.

6. The method according to claim 1, wherein $F_1^I$ is based on a difference in electrochemical potential between materials of an interface.

7. The method according to claim 1, wherein $$RCI_{Material} = RCI_{Base} \times F_{Prohibit} \times F_{ST} \times F'_{Coating} \times F_{Moisture} \times F_{Protective} \times F_{Adverse}, \text{ wherein}$$

$F_{Prohibit}$ is a value between about 1 and about 100 that is empirically assigned based on whether the material is prohibited, $F_{ST}$ is a value between about 0 and about 1 that is empirically assigned based on the presence and type of a surface treatment, $F'_{Coating}$ is a value between about 0 and about 10 that is empirically assigned based on the presence and type of coating, $F_{Moisture}$ is a value between about 0 and about 10 that is empirically assigned based on whether the material is exposed to moisture, $F_{Protective}$ is a value between about 0 and about 1 that is empirically assigned based on whether the material is exposed to protective conditions, and $F_{Adverse}$ is a value between about 0 and about 10 that is empirically assigned based on whether the material is exposed to adverse conditions.

8. The method according to claim 7, wherein $F'_{Coating}$ is empirically assigned further based on a presence and type of primer on the material, the location of the material in the assembly, and a type of damage that the material is exposed to in the location.

9. The method according to claim 7, wherein $F_{Moisture}$ is empirically assigned further based on a location of the material in the assembly, whether drainage is present in the location, and whether the material is functioning as a fastener.

10. The method according to claim 7, wherein $F_{Protective}$ is empirically assigned based on whether the material is immersed in oil, immersed in fuel, in a pressurized environment, or in a protected environment.

11. The method according to claim 7, wherein $F_{Adverse}$ is empirically assigned based on whether the material is exposed to salt, ultraviolet light, deicing solution, waste water, exhaust, or heat.

12. The method according to claim 7, wherein at least one of $F_{Protective}$ or $F_{Adverse}$ is equal to 1.

13. The method according to claim 1, wherein $$RCI_{Interface} = RCI_{Material_{Max}} \times F_{galvanic} \times F_{Sealant} \times F_{small},$$
wherein $F_{galvanic}$ is a value between about 0 and about 10 that is empirically assigned based on the difference in electrochemical potential between the two materials of the interface, $F_{Sealant}$ is a value between about 0 and about 1 that is empirically assigned based on whether any of the materials are electrochemically isolated by a sealant, $F_{small}$ is a value between about 1 and about 10 that is empirically assigned based on the relative difference in the sizes of the materials.

14. The method of claim 1, wherein $RCI_{Assembly}$ is from about 0 to about 100.

15. The method of claim 1, wherein an assembly having an $RCI_{Assembly}$ equal to about 100 is predicted to be more likely to corrode than an assembly having an $RCI_{Assembly}$ equal to about 0.

16. The method of claim 1, wherein the material corrosion factors and interface corrosion factors are stored in electronic format.

17. The method of claim 1, where said assembly is a component of an aerospace vehicle.

18. A computer program product embodied on a computer readable medium and configured to execute by microprocessor a method for predicting corrosion potential comprising computer instructions for executing the steps of providing an assembly comprising
from 1 to i materials, and
from 0 to j interfaces, wherein each interface is a contact between any two materials;

calculating an $RCI_{Material}$ value for each material according to Formula I:

$$RCI_{Material} = RCI_{Base} \times f_M(F_1^M, \ldots F_n^M) \quad \text{[Formula I]}$$

wherein
$RCI_{Base}$ is a real number or a function that may be evaluated to a real number that is unique for the material,
$f_M$ is a first scalar function, and
$F_1^M$ to $F_n^M$ are material corrosion factors selected from the set of real numbers or functions that may be evaluated to real numbers;

calculating an $RCI_{Interface}$ value for each interface according to Formula II:

$$RCI_{Interface} = RCI_{Material_{Max}} \times f_I(F_1^I, \ldots F_m^I) \quad \text{[Formula II]}$$

wherein
$RCI_{Material_{Max}}$ is the largest $RCI_{Material}$ of the materials in the interface as calculated according to Formula I,
$f_I$ is a second scalar function, and
$F_1^I$ to $F_m^I$ are interface corrosion factors selected from the set of real numbers or functions that may be evaluated to real numbers; and calculating an $RCI_{Assembly}$ value according to Formula III:

$$RCI_{Assembly} = f_A\{(RCI_{Material})_1, \ldots (RCI_{Material})_i, \ldots (RCI_{Interface})_j\} \quad \text{[Formula III]}$$

wherein
$f_A$ is a third scalar function,
each $RCI_{Material}$ value is calculated according to Formula I, and
each $RCI_{Interface}$ value is calculated according to Formula II;
wherein the magnitude of $RCI_{Assembly}$ is based on the corrosion potential of said assembly.

19. The computer program product according to claim 18, wherein said material corrosion factors and said interface corrosion factors include protective corrosion factors and adverse corrosion factors, wherein said protective corrosion factors are selected from a first set consisting of real numbers or functions that may be evaluated to real numbers and said adverse corrosion factors are selected from a second set consisting of real numbers or functions that may be evaluated to real numbers, wherein said first set and said second set are orthogonal.

20. The computer program product according to claim 19, wherein said first set consists of real numbers less than or equal to one, and said second set consists of real numbers greater than or equal to one.

21. The method of claim 18, wherein said material corrosion factors and said interface corrosion factors are stored in electronic format.

22. A method of inspecting an aerospace vehicle comprising the steps of determining an RCI for a component of an aerospace vehicle according to the method of claim 1; inspecting said component for corrosion; and thereafter re-inspecting said component for corrosion, wherein the amount of time between said inspecting step and said re-inspecting step is based on the magnitude of the RCI for said component.

23. A method of preparing a maintenance schedule for an aerospace vehicle comprising a step of calculating an RCI value for a component of said aerospace vehicle according to the method of claim 1 and assigning the frequency of scheduled inspection or maintenance of said component based on said RCI value.

24. A method comprising a step of calculating an RCI value for a component according to the method of claim 1 and selecting said component based on said RCI value for use in the manufacture or repair of an aerospace vehicle.

25. The method of claim 24, wherein said RCI value is within a predetermined range.

26. An aerospace vehicle having a plurality of components, wherein each component has an RCI value within a predetermined range calculated according to claim 1.

27. A component for an aerospace vehicle having an RCI value calculated according to claim 1.

28. The method of claim 1, wherein said assembly is a component of an airplane, oil drilling equipment, an ocean-going cargo ship, a railroad or railcar, an automobile, a bridge; a building; a pressure vessel, a petrochemical plant, an engine, or a tank.

* * * * *